(12) United States Patent
Kim et al.

(10) Patent No.: US 8,648,111 B2
(45) Date of Patent: Feb. 11, 2014

(54) N1-2-THIOPHENE-2-YLETHYL-N2-SUBSTITUTED BIGUANIDE DERIVATE, PREPARATION METHOD THEREOF, AND PHARMACEUTICAL COMPOSITION CONTAINING THE SAME AS ACTIVE INGREDIENTS

(75) Inventors: Sung Wuk Kim, Seongnam-si (KR); Sung Soo Jun, Seongnam-si (KR); Hyae Gyeong Cheon, Daejeon-si (KR); Kwang Rok Kim, Daejeon-si (KR); Sang Dal Rhee, Daejeon-si (KR); Won Hoon Jung, Daejeon-si (KR); Jong Cheol Lee, Daejeon-si (KR)

(73) Assignees: Hanall Biopharma Co., Ltd., Daejeon-Si (KR); Korea Research Institute of Chemical Technology, Daejeon-Si (KR)

( * ) Notice: Subject to any disclaimer, the term of this patent is extended or adjusted under 35 U.S.C. 154(b) by 290 days.

(21) Appl. No.: 13/123,296

(22) PCT Filed: Oct. 13, 2009

(86) PCT No.: PCT/KR2009/005856
§ 371 (c)(1),
(2), (4) Date: Apr. 8, 2011

(87) PCT Pub. No.: WO2010/044582
PCT Pub. Date: Apr. 22, 2010

(65) Prior Publication Data
US 2011/0196015 A1    Aug. 11, 2011

(30) Foreign Application Priority Data
Oct. 13, 2008  (KR) .................. 10-2008-0100221

(51) Int. Cl.
*A61K 31/38*    (2006.01)
*C07D 333/20*    (2006.01)

(52) U.S. Cl.
USPC ............................................ 514/438; 549/74

(58) Field of Classification Search
None
See application file for complete search history.

(56) References Cited

U.S. PATENT DOCUMENTS 2,961,377 A * 11/1960 Shapiro et al. ............... 514/635
2004/0092495 A1   5/2004 Moinet et al.

FOREIGN PATENT DOCUMENTS

KR  10-2003-0085558 A   11/2003
KR  10-2008-0086442 A    9/2008

OTHER PUBLICATIONS

Sherr. Cancer Cell, 2002, 2, 103-112.*
"Type 1 Diabetes-Prevention", http://diabetes.webmd.com/tc/type-1-diabetes-prevention, accessed Dec. 12, 2008.*
"Glucose Metabolism Disorders", http://www.nlm.nih.gov/cgi/mesh/2013/MB_cgi?mode=&index=22078&field=all&HM=&, accessed Mar. 19, 2013.*

* cited by examiner

*Primary Examiner* — Noble Jarrell
(74) *Attorney, Agent, or Firm* — Sughrue Mion, PLLC

(57) ABSTRACT

The present invention provides an N1-2-thiophen-2-ylethyl-N2-substituted biguanide derivative of formula (I) or a pharmaceutically acceptable salt thereof, a method for preparing same, and a pharmaceutical composition comprising same as an active ingredient. The inventive N1-2-thiophen-2-ylethyl-N2-substituted biguanide derivative exhibits improved blood glucose level- and lipid level-lowering effects even with a reduced dosage as compared to conventional drugs, and thus, it is useful for preventing or treating diabetes, metabolic syndromes such as insulin-independent diabetes, obesity and atherosclerosis, or a P53 gene defect-related cancer.

12 Claims, No Drawings

N1-2-THIOPHENE-2-YLETHYL-N2-SUBSTITUTED BIGUANIDE DERIVATE, PREPARATION METHOD THEREOF, AND PHARMACEUTICAL COMPOSITION CONTAINING THE SAME AS ACTIVE INGREDIENTS

CROSS REFERENCE TO RELATED APPLICATION

This application is a National Stage of International Application No. PCT/KR2009/005856 filed Oct. 13, 2009, claiming priority based on Korean Patent Application No. 10-2008-100221, filed Oct. 13, 2008, the contents of all of which are incorporated herein by reference in their entirety.

TECHNICAL FIELD

The present invention relates to N1-2-thiophen-2-ylethyl-N2-substituted biguanide derivatives which exhibit improved blood glucose level- and lipid level-lowering effects even with a reduced dosage as compared to conventional drugs, a method for preparing same, and a pharmaceutical composition comprising same as an active ingredient.

BACKGROUND ART

Diabetes is a disease characterized by continuous high blood glucose levels. The major conditions of diabetes are carbohydrate metabolism abnormality and lipid metabolism abnormality, and systemic complications thereof grow worse due to blood flow disturbance caused by high blood glucose levels and due to a decrease in sugar utilization. Such diabetic conditions are caused by the deficiency of hormone insulin, which regulates carbohydrate and lipid metabolisms, or insulin resistance. Diabetes caused by insulin resistance is called "type 2 diabetes".

Type 2 diabetes is induced from a state in which insulin does not exhibit a function of transporting glucose into cells due to the decreases of insulin receptors or due to the deficiency of signal transduction pathways through insulin receptors, i.e., a condition in which the body becomes resistant to insulin secreted from the pancreas. In other words, Type 2 diabetes suffers from direct destruction of blood vessels and severe metabolic syndromes due to hyperinsulinemia.

Many kinds of anti-diabetic drugs have been used to treat type 2 diabetes. However, the drugs excluding biguanide metformin do not show satisfactory effects on the prevention of important complications including visual loss, heart failure, stroke, renal failure, peripheral neuropathy, foot ulcer and the like, although they are somewhat effective in lowering blood glucose levels. For example, sulfonylurea-based drugs, which act to lower blood glucose levels by enforcing insulin to be secreted from the pancreas, have problems in that their effects rapidly disappear and they induce abnormal lipid metabolism, thereby promoting arteriosclerosis, increasing bodyweight and causing brain injuries due to low blood glucose levels. Moreover, as glitazone-based drugs give an effect only on insulin resistance mainly in adipose tissues, they must be used in combination with metformin. In addition, close attention should be paid to the use of the glitazone-based drugs because the drugs may cause side effects such as retinal vascular occlusion.

Metformin, the only drug that has the same effect as that of insulin, does not cause a low blood glucose problem, solves a problem of insulin resistance in adipose, liver and muscular tissues, and exhibits improved blood glucose level- and glycosylated hemoglobin level-lowering actions. Particularly, it has been reported that metformin activates AMPK (AMP-activated protein kinase), and thus has various effects of normalizing blood glucose levels, enhancing lipid conditions, normalizing irregular menstruation, ovulation and pregnancy, treating fatty liver, and even preventing cancers.

Metformin is generally administered three times a day, and its dosage per one administration is more than about 500 mg. Thus, in order to make sustained-release tablets to be administered once a day, tablets containing at least 1500 mg of metformin are required. However, it is difficult to take such tablets due to its very large size. In addition, currently commercially available sustained-release tablets contain only about 750 mg of metformin per one tablet, and thus, at least two tablets should be administered once at a 24 hr interval. Therefore, there exists a need to develop preparations which exhibit improved blood glucose level- and lipid level-lowering effects, thereby being capable of reducing its daily dosage.

DISCLOSURE OF INVENTION

Accordingly, it is a primary object of the present invention to provide a novel compound which exhibits improved blood glucose level- and lipid level-lowering effects even with a reduced dosage as compared to conventional drugs, and a method for preparing same.

It is another object of the present invention to provide a pharmaceutical composition comprising said compound as an active ingredient, for preventing or treating diabetes, metabolic syndromes such as insulin-independent diabetes, obesity and atherosclerosis, or a P53 gene defect-related cancer.

In accordance with one aspect of the present invention, there is provided an N1-2-thiophen-2-ylethyl-N2-substituted biguanide derivative of formula (I) or a pharmaceutically acceptable salt thereof:

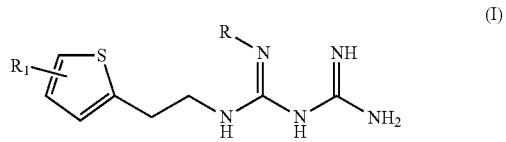

wherein,
R is $C_1$-$C_8$alkyl; allyl; $C_1$-$C_8$alkoxyalkyl; $C_3$-$C_7$cycloalkyl; $C_3$-$C_7$cycloalkyl$C_1$-$C_3$alkyl; substituted or non-substituted phenyl or phenyl$C_1$-$C_3$alkyl; substituted or non-substituted naphthyl or naphthyl$C_1$-$C_3$alkyl; or adamantyl; and
$R_1$ is hydrogen or $C_1$-$C_6$alkyl.

In accordance with another aspect of the present invention, there is provided a method for preparing the compound of formula (I).

In accordance with a further aspect of the present invention, there is provided a pharmaceutical composition for preventing or treating diabetes, comprising the compound of formula (I) as an active ingredient.

In accordance with a further aspect of the present invention, there is provided a pharmaceutical composition for preventing or treating metabolic syndromes, comprising the compound of formula (I) as an active ingredient.

In accordance with a further aspect of the present invention, there is provided a pharmaceutical composition for preventing or treating a P53 gene defect-related cancer, comprising the compound of formula (I) as an active ingredient.

ADVANTAGEOUS EFFECTS

An N1-2-thiophen-2-ylethyl-N2-substituted biguanide derivative of formula (I) of the present invention is capable of exhibiting improved blood glucose level- and lipid level-lowering effects even with a reduced dosage, and thus, it is useful for preventing or treating diabetes, metabolic syndromes such as insulin-independent diabetes, obesity and atherosclerosis, or a P53 gene defect-related cancer.

BEST MODE FOR CARRYING OUT THE INVENTION

In the compound of formula (I) of the present invention, unless otherwise stated or indicated, the term "$C_1$-$C_8$alkyl" used herein denotes either a linear or branched alkyl group. Examples of said alkyl include methyl, ethyl, n-propyl, isopropyl, n-butyl, isobutyl, sec-butyl, tert-butyl, n-pentyl, n-hexyl, n-heptyl, and t-octyl.

Preferred examples of the term "$C_1$-$C_8$alkoxyalkyl" used herein include methoxymethyl, methoxyethyl, methoxyethoxyethyl, ethoxymethyl, and octyloxymethyl.

Examples of the term "$C_3$-$C_7$cycloalkyl" used herein include cyclopropyl, cyclobutyl, cyclopentyl, cyclohexyl, and cycloheptyl.

Preferred examples of the term "$C_3$-$C_7$cycloalkyl$C_1$-$C_3$alkyl" used herein include cyclopropylmethyl, cyclobutylmethyl, cyclopentylmethyl, cyclohexylmethyl, cyclopropylethyl, cyclobutylethyl, cyclopentylethyl, cyclohexylethyl, cyclopropylpropyl, cyclobutylpropyl, cyclopentylpropyl, and cyclohexylpropyl.

Preferred examples of the term "substituted or non-substituted phenyl or phenyl$C_1$-$C_3$alkyl" include benzyl, phenyl, naphthyl, 1-phenylethyl, 2-phenylethyl, 1-phenylpropyl, 2-phenylpropyl, and 3-phenylpropyl, which have either substituent(s) or no substituent. The number of the substituent(s) may be one to six, preferably one to three, and two or more substituents may be each other same or different. The substituent(s) may combine to any one of chemically allowable positions in phenyl, and examples thereof include halogen, hydroxy, nitro, cyano, $C_1$-$C_6$alkyl, $C_1$-$C_6$haloalkyl, $C_1$-$C_6$cycloalkyl, $C_6$-$C_{10}$aryl, $C_6$-$C_{10}$aryloxy, $C_1$-$C_6$alkoxy, $C_1$-$C_6$haloalkoxy, $C_3$-$C_6$cycloalkyloxy, $C_1$-$C_7$alkanoyl, carboxy, carbamoyl, alkylamino, $C_2$-$C_7$sulfonate, sulfonamide, and $C_1$-$C_6$alkylthio.

Preferred examples of the term "substituted or non-substituted naphthyl or naphthyl$C_1$-$C_3$alkyl" include 1-naphthylmethyl, 2-naphthylmethyl, 1-naphthylethyl, and 2-naphthylethyl, which have either substituent(s) or no substituent, wherein the substituent is the same as that of "phenyl or phenyl$C_1$-$C_3$alkyl" as described above.

Preferred examples of the term "$C_1$-$C_6$alkyl" include methyl, ethyl, propyl, butyl, pentyl, and hexyl.

Among the compounds of formula (I) of the present invention, preferred are those wherein R is ethyl, t-octyl, 1-naphthyl, hexyl, methyl, cyclohexyl, t-butyl, benzyl, 2-ethylphenyl, propyl, 3-trifluoromethylphenyl, 4-methoxyphenyl, 2,5-dimethoxyphenyl, 3,4,5-trimethoxyphenyl, 4-fluorophenyl, 4-methylphenyl, phenyl, cyclopentyl, cycloheptyl, pentyl, methoxyethyl, butyl, 3-methylphenyl, 4-t-butylphenyl, 3-hexylphenyl, 4-methoxyphenyl, 2,5-dimethoxyphenyl, 3,5-dimethoxyphenyl, 4-bromophenyl, 3-bromophenyl, 3-phenylphenyl, 3-phenoxyphenyl, 4-bromobenzyl, 4-methoxybenzyl, 3,5-dichlorophenyl, 4-methylbenzyl, isopropyl, isobutyl, cyclopropylmethyl, or allyl; and $R_1$ is hydrogen, 3-methyl, or 5-ethyl.

The pharmaceutically acceptable salt of the inventive compound of formula (I) includes salts with organic acids (for example, formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, benzenesulfonic acid, p-toluenesulfonic acid, and methansulfonic acid) and salts with inorganic acids (for example, hydrochloric acid, bromic acid, sulfuric acid, phosphoric acid, nitric acid, carbonic acid, and boric acid). The above-mentioned acid addition salts are prepared by a general salt preparation method comprising: (a) mixing the compound of formula (I) directly with an acid; (b) dissolving one of them in a solvent or a water-containing solvent and mixing the solution with the other one; or (c) placing the compound of formula (I) in either a solvent or an acid in a water-containing solvent and mixing them.

If the compound of formula (I) has an acidic group, for example, a carboxy group and a sulfonic acid group, it becomes an amphoteric salt. Examples of such a salt may include alkali metal salts (for example, sodium and potassium salts), alkaline earth metal salts (for example, calcium and magnesium salts), salts with inorganic acids (for example, aluminum and ammonium salts), basic addition salts (for example, salts with organic acids such as trimethylamine, triethylamine, pyridine, picoline, ethanolamine, diethanolamine, triethanolamine, dicyclohexylamine, and N,N'-dibenzylethylenediamine), and a mixture thereof. Also, salts of the compound of formula (I) may be salts with basic amino acids (for example, arginine, lysine and ornithine), or with acidic amino acids (for example, aspartic acid). The salt of the compound of formula (I) is preferably a pharmaceutically acceptable salt, more preferably an acid addition salt, even more preferably acetate, hydrochloride, hydrobromide, methane sulfonate, malonate, or oxalate.

In one embodiment, the inventive compound of formula (I) can be prepared by:

1) subjecting a compound of formula (II) to a reaction with $NaBH_4$ in a solvent to form a compound of formula (III);

2) subjecting the compound of formula (III) to a reaction with thionyl chloride in an organic solvent to form a compound of formula (IV);

3) subjecting the compound of formula (IV) to a reaction with sodium cyanide in DMSO to form a compound of formula (V);

4) subjecting the compound of formula (V) to a reaction with sodium borohydride and a nickel chloride hydrate in a solvent to form a compound of formula (VI);

5) subjecting the compound of formula (VI) to a reaction with R-isothiocyanate (RNCS) in an organic solvent in the presence of a base to form a compound of formula (VIII); and 6) allowing the compound of formula (VIII) to be kept in a guanidine solution in the presence of mercuric oxide:

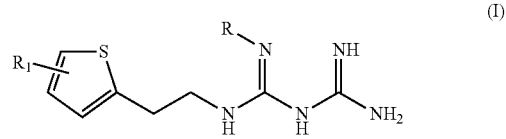
(I)

(II)
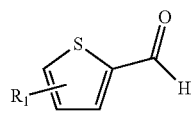

(III)
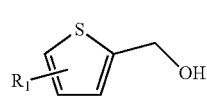

(IV)
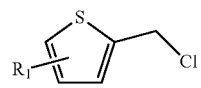

(V)
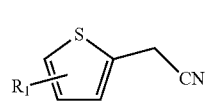

(VI)
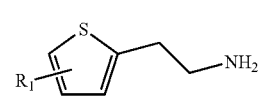

(VIII)
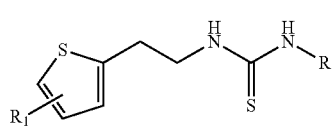

wherein, R and $R_1$ have the same meanings as defined in formula (I).

In another embodiment, the inventive compound of formula (I) can be prepared by:
1) subjecting a compound of formula (II) to a reaction with $NaBH_4$ in a solvent to form a compound of formula (III);
2) subjecting the compound of formula (III) to a reaction with thionyl chloride in an organic solvent to form a compound of formula (IV);
3) subjecting the compound of formula (IV) to a reaction with sodium cyanide in DMSO to form a compound of formula (V);
4) subjecting the compound of formula (V) to a reaction with sodium borohydride and a nickel chloride hydrate in a solvent to form a compound of formula (VI);
5) subjecting the compound of formula (VI) to a reaction with ethyl chloroformate in an organic solvent in the presence of carbon disulfide and a base to form a compound of formula (VII);
6) subjecting the compound of formula (VII) to a reaction with $NH_2R$ in a solvent in the presence of a base to form a compound of formula (VIII); and
7) allowing the compound of formula (VIII) to be kept in a guanidine solution in the presence of mercuric oxide:

(I)
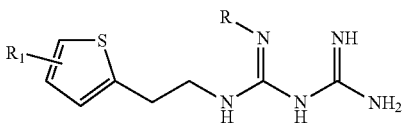

(II)
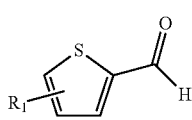

(III)
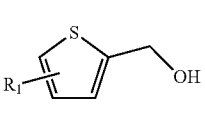

(IV)
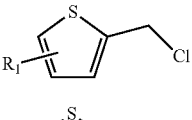

(V)
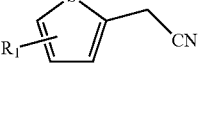

(VI)

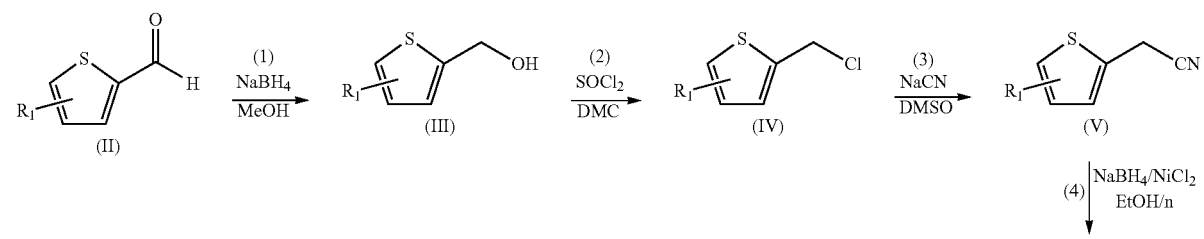

(VII)

(VIII)

wherein, R and $R_1$ have the same meanings as defined in formula (I).

The above preparation methods are shown in Reaction Scheme 1 and procedures thereof are described in detail as follows:

Reaction Scheme 1

-continued

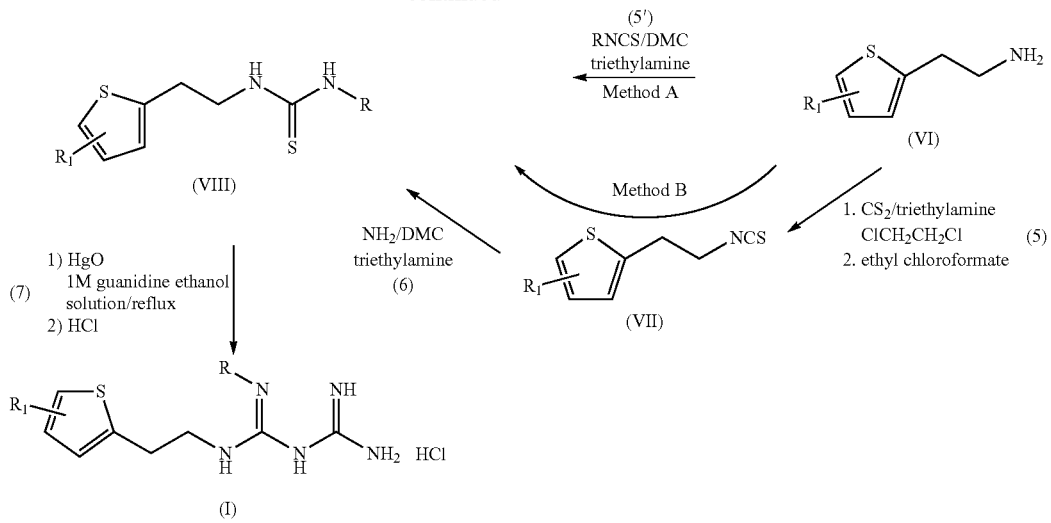

wherein, R and $R_1$ have the same meaning as defined in formula (I).

In step (1) of Reaction Scheme 1, the substituted thiophene carboxaldehyde compound of formula (II) as a starting material is subjected to a reaction with sodium borohydride ($NaBH_4$) in a solvent (for example, methanol, ethanol, propanol, isopropanol, butanol, tetrahydrofuran, acetonitrile, N,N-dimethylformamide or dimethylsulfoxide) at a temperature ranging from 0° C. to a reflux temperature to obtain the alcohol derivative of formula (III). The sodium borohydride is used in an amount ranging from 1 to 3 mole equivalents based on the amount of the compound of formula (II).

The compound of formula (II) used as a starting material in step (1) is commercially available and can be easily synthesized by a conventional method.

In step (2) of Reaction Scheme 1, the compound of formula (III) obtained in step (1) is subjected to a reaction with thionyl chloride in an organic solvent (for example, dichloromethane, dichloroethane or N,N-dimethylformamide) at a temperature ranging from 0° C. to a reflux temperature to obtain the chloride derivative of formula (IV). The thionyl chloride is used in an amount ranging from 3 to 10 mole equivalents based on the amount of the compound of formula (III).

In step (3) of Reaction Scheme 1, the compound of formula (IV) obtained in step (2) is subjected to a reaction with sodium cyanide in DMSO at room temperature to obtain the cyanide derivative of formula (V). The sodium cyanide is used in an amount ranging from 2 to 4 mole equivalents based on the amount of the compound of formula (IV).

In step (4) of Reaction Scheme 1, the compound of formula (V) obtained in step (3) is subjected to a reaction with sodium borohydride and a nickel chloride hydrate in a solvent (for example, methanol, ethanol, propanol, isopropanol, butanol, tetrahydrofuran, acetonitrile, N,N-dimethylformamide or dimethylsulfoxide) at a room temperature to obtain the substituted thiophene ethylamine derivative of formula (VI). The sodium borohydride and a nickel chloride hydrate may be used in amounts ranging from about 3 to 5 mole equivalents and from 1 to 2 mole equivalents, respectively, based on the amount of the compound of formula (V).

Further, the thiourea compound of formula (VIII) which is used as an intermediate in the synthesis of the compound of formula (I) is obtained by: (A) in case isothiocyanate (RNCS) having a substituent R is commercially available, subjecting the thiophene ethylamine compound of formula (VI) to a reaction with RNCS in a solvent in the presence of a base (step (1)); or (B) in case RNCS having a substituent R is not commercially available, subjecting the compound of formula (VI) to a reaction with ethyl chloroformate in a solvent in the presence of carbon disulfide and a base to form the compound of formula (VII) (step (1')), and subjecting the compound of formula (VII) to a reaction with $NH_2R$ in an organic solvent in the presence of a base (step (2)).

Examples of the base which may be used in steps (5), (5') and (6) for the synthesis of the thiophene ethylamine compound of formula (VI) include triethylamine, trimethylamine, diisopropylethylamine, and a mixture thereof; and examples of the organic solvent include dichloromethane, dichloroethane, N,N-dimethylformamide, and a mixture thereof. The reactions in steps (5), (5') and (6) may be conducted at a temperature ranging from 0° C. to room temperature. In steps (5) and (5'), the carbon disulfide, base and ethyl chloroformate may be used in amounts ranging from about 1 to 2 mole equivalents, respectively, based on the amount of the compound of formula (VI).

In step (7) of Reaction Scheme 1, the thiourea compound of formula (VIII) obtained in step (2) is dissolved in a mixture of mercuric oxide and an appropriate organic solvent (e.g., ethylalcohol, methylalcohol or N,N-dimethylformamide), and 1M guanidine ethanol solution is added to the resulting solution, which is refluxed. The mercuric oxide and 1M guanidine ethanol solution may be used in amounts ranging from about 1 to 2 mole equivalents and from 1 to 3 mole equivalents, respectively, based on the amount of the compound of formula (VIII). The reaction in step (3) may be conducted at a temperature ranging from room temperature to the reflux temperature of the solvent used. For instance, in case of using a N,N-dimethylformamide solvent, the reaction temperature is in the range of room temperature and 100° C. After completion of the reaction, the resulting solution is subjected to filtration, and then pH of the filtrate is preferably adjusted to the range of about 4 to 5 by using an acid such as hydrochloric acid. The resulting solution is concentrated and purified to obtain the compound of formula (I) or a pharmaceutically acceptable salt thereof.

The compound of formula (I) or a pharmaceutically acceptable salt thereof thus obtained exhibits improved blood glucose level- and lipid level-lowering effects even with a reduced dosage as compared to conventional drugs, and therefore, it is useful for preventing or treating metabolic syndromes.

Accordingly, the present invention provides a pharmaceutical composition for preventing or treating metabolic syndromes, comprising the compound of formula (I) or a pharmaceutically acceptable salt thereof as an active ingredient. Examples of the metabolic syndrome include insulin-independent diabetes, obesity and atherosclerosis.

In addition, the present invention provides a pharmaceutical composition for preventing or treating diabetes, comprising the compound of formula (I) or a pharmaceutically acceptable salt thereof as an active ingredient.

Furthermore, the present invention provides a pharmaceutical composition for preventing or treating a P53 gene defect-related cancer, comprising the compound of formula (I) or a pharmaceutically acceptable salt thereof as an active ingredient.

The compound of formula (I) or its pharmaceutically acceptable salt may be administered as it is or in a form of a pharmaceutical composition in combination with at least one pharmaceutically acceptable additive.

The pharmaceutically acceptable additive may be selected in consideration of the administration route and formulation purpose from the group consisting of stabilizing agents, binders, bases, sugar-containing coating agents, excipients, disintegrants, dissolution-serving agents, viscosity-controlling agents, coating agents, emulsifiers, pH controlling agents, isotonic agents, polishing agents, dispersing agents, sweeteners, taste-enhancing agents, wetting agents, soft capsule bases, hard capsule bases, plasticizers, preservatives, antioxidants, solvents, lubricants, adhesives, surfactants, shielding agents, coloring agents, dispersing agents, topical analgesia, buffers, refreshing agents, dissolving agents, and a mixture thereof.

The inventive pharmaceutical composition may be formulated in a form suitable for a desired use and purpose by using a conventional formulation technique.

The inventive pharmaceutical composition may be orally administered in the form of tablets, powders, granules, pills, troches, capsules or solutions. Also, the pharmaceutical composition may be parenterally administered in the form of injection solutions, suppositories, ointments, topical solutions, pastes, cataplasmas, liniments or plasters.

The suitable daily single dosage for oral administration of the inventive compound of formula (I) or a pharmaceutically acceptable salt thereof is preferably in the range of 0.5 and 150 mg/kg body weight based on a 60 kg adult man. Such a dosage can be determined depending on various factors including the age and condition of the patient, and the chosen route of administration. In certain cases, either amount less than or greater than the above dosage can be administered.

The following Examples are intended to further illustrate the present invention without limiting its scope.

Example 1

Preparation of N1-(thiophen-2-ylethyl)-N2-ethyl biguanide hydrochloride (1-1) Preparation of 1-ethyl-3-(2-(thiophen-2-yl)ethyl)thiourea Ethyl isothiocyanate (1.3 g, 15.0 mmol) was slowly added dropwise to a solution of thiopheneethylamine (1.3 g, 10.2 mmol) in dichloromethane (150 mL). Triethyl amine (3.8 mL, 20.4 mmol) was added dropwise to the mixture and stirred at room temperature for 2 h. After completion of the reaction, pH of the resulting solution was adjusted to about 7 using aqueous 1N HCl, to which water was added. The resulting mixture was extracted with dichloromethane. The residue was purified by flash column chromatography (ethyl acetate:hexanes=1:3), to give the title compound (1.9 g, 89%).

$^1$H NMR (300 MHz, CDCl$_3$) δ 7.45 (br s, 1H), 7.42 (br s, 1H), 7.39-7.30 (m, 1H), 6.95-6.97 (m, 1H), 6.87-6.88 (m, 1H), 3.60-3.50 (m, 2H), 3.40-3.25 (m, 2H), 3.00 (t, 2H, J=7.4), 1.02 (t, 3H, J=7.2)

(1-2) Preparation of N1-(thiophen-2-ylethyl)-N2-ethyl biguanide hydrochloride

The compound obtained in step (1-1) (1.1 g, 5.10 mmol) was dissolved in ethanol (15 mL), and mercuric(II)oxide (2.2 g, 10.2 mmol) was added thereto. Guanidine (15 mL, 1.0 M in EtOH, 15.3 mmol) was slowly added dropwise to the reaction mixture and refluxed for 12-24 h. The resulting mixture was cooled and filtered with a Celite filter. pH of the filtrate was adjusted to about 4 to 5 using aqueous 2N HCl. The resulting mixture was concentrated and the residue was purified by flash column chromatography (dichloromethane:methanol=9:1), to obtain the title compound (0.21 g, 15%).

$^1$H NMR (300 MHz, DMSO-d$_6$) δ 7.33-7.34 (m, 1H), 6.85-6.94 (m, 2H), 3.28-3.32 (m, 2H), 2.96-3.11 (m, 4H), 0.99-1.04 (m, 3H); mp 128.0-131.7° C.

Example 2

Preparation of N1-2-(thiophen-2-ylethyl)-N2-t-octyl biguanide hydrochloride (2-1) Preparation of 2-(2-isothiocyanatoethyl)thiophene Thiopene ethylamine (4.60 mL, 39.31 mmol) and triethyl amine (5.00 mL, 39.31 mmol) were dissolved in 1,2-dichloroethane (25 mL), and the resulting mixture was cooled to 0° C. A solution of carbon disulfide (2.36 mL, 39.31 mmol) in 1,2-dichloroethane (50 mL) was added dropwise thereto over 15 min. The reaction mixture was allowed to warm to room temperature and re-cooled to 0° C., to which ethyl chloroformate (4.27 mL, 31.39 mmol) was added dropwise. The reaction mixture was stirred at room temperature for about 1-2 h, and water (150 mL) and aqueous 2N sodium hydroxide (75 mL) were sequentially added thereto. The resulting mixture was extracted with dichloromethane. The extract was washed with water and brine, dried over sodium sulfate, and concentrated, to obtain the yellow title compound in a liquid form (5.37 g, 80.75%).

1H NMR (300 MHz, CDCl$_3$) δ 7.22 (dd, 1H, J=5.1, 1.2 Hz, Thiopene), 6.98 (dd, 1H, J=5.1, 3.4 Hz, Thiopene), 6.93-6.91 (m, 1H, Thiopene), 3.76 (t, 2H, J=6.7 Hz, CH$_2$), 3.22 (t, 2H, J=6.8 Hz, CH$_2$)

(2-2) Preparation of 1-t-octyl-3-(2-(thiophen-2-yl)ethyl)thiourea

The procedure of step (1-1) of Example 1 was repeated except for using the compound obtained in step (2-1) (2.5 g, 15.0 mmol) and t-octyl amine (1.6 mL, 10.2 mmol), to obtain the title compound (2.5 g, 83%).

1H NMR (300 MHz, DMSO-d$_6$) δ 7.33 (m, 1H), 7.31 (br s, 1H), 7.19 (br s, 1H), 6.93 (m, 1H), 6.84 (m, 1H), 3.57 (m, 2H), 2.96 (t, 2H, J=7.0), 1.97 (s, 2H), 1.97 (s, 6H), 0.92 (s, 9H),

(2-3) Preparation of N1-2-(thiophen-2-ylehtyl)-N2-t-octyl biguanide hydrochloride The procedure of step (1-2) of Example 1 was repeated except for using the compound obtained in step (2-2) (1.5 g, 5.10 mmol), to obtain the title compound (0.31 g, 17%).

$^1$H NMR (300 MHz, DMSO-$d_6$) δ 7.33-7.36 (m, 1H), 6.89-6.96 (m, 2H), 3.20-3.21 (m, 2H), 2.97-2.99 (m, 2H), 1.28-1.30 (m, 6H), 0.90-0.93 (m, 1H)

EXAMPLES 3 TO 44

The procedure of Example 1 was repeated except for using an isothiocyanate compound, which corresponds to a desired compound, instead of ethyl isothiocyanate in step (1-1) of Example 1, to obtain the title compounds of Examples 3-5, 7, 8, 10-13, 20, 23, 25, 26, 41 and 42.

Alternatively, the procedure of Example 2 was repeated except for using an amine compound which corresponds to a desired compound, instead of t-octyl amine, in step (2-2) of Example 2, to obtain the title compounds of Examples 6, 9, 14-19, 21, 22, 24, 27-40, 43 and 44.

Example 3

Preparation of N1-2-(thiophen-2-ylethyl)-N2-1-naphthyl biguanide hydrochloride $^1$H NMR (300 MHz, DMSO-$d_6$) δ 7.71-7.72 (m, 1H), 7.28-7.50 (m, 5H), 6.79-6.90 (m, 4H), 3.3.37-3.33 (m, 2H), 2.97-3.03 (t, 2H, J=6.9).

Example 4

Preparation of N1-2-(thiophen-2-ylethyl)-N2-hexyl biguanide hydrochloride $^1$H NMR (300 MHz, DMSO-$d_6$) δ 7.25-7.35 (m, 1H), 6.81-6.88 (m, 2H), 3.20-3.24 (m. 2H), 2.88-3.05 (m, 4H), 2.89-2.99 (m, 4H), 1.11-1.32 (m, 4H), 0.75-0.78 (m, 3H).

Example 5

Preparation of N1-2-(thiophen-2-ylethyl)-N2-methyl biguanide hydrochloride $^1$H NMR (300 MHz, DMSO-$d_6$) δ 7.31-7.32 (m, 1H), 6.87-6.95 (m, 2H), 3.27-3.32 (t, 2H, J=7.2), 2.93-2.98 (t, 2H, J=7.2), 2.63 (s, 3H); Mass (ESI) m/z 226.7 (M$^+$).

Example 6

Preparation of N1-2-(thiophen-2-ylethyl)-N2-cyclohexyl biguanide hydrochloride $^1$H NMR (300 MHz, DMSO-$d_6$) δ 7.36-7.39 (m, 1H), 6.90-7.00 (m, 2H), 3.25-3.24 (m, 2H), 2.97-3.05 (m, 2H), 2.23-2.28 (m, 1H), 1.66-1.90 (m, 5H), 1.14-1.18 (m, 5H); Mass (ESI) m/z 294.7 (M$^+$).

Example 7

Preparation of N1-2-(thiophen-2-ylethyl)-N2-t-butyl biguanide hydrochloride $^1$H NMR (300 MHz, DMSO-$d_6$) δ 7.38-7.42 (m, 1H), 6.94-7.01 (m, 2H), 3.25-3.24 (m, 2H), 2.99-3.04 (m, 2H), 1.25-1.30 (m, 9H); Mass (ESI) m/z 268.7 (M$^+$).

Example 8

Preparation of N1-2-(thiophen-2-ylethyl)-N2-t-benzyl biguanide hydrochloride $^1$H NMR (300 MHz, DMSO-$d_6$) δ 7.24-7.48 (m, 6H), 6.90-7.01 (m, 2H), 4.34-4.35 (m, 2H), 2.98-3.22 (m, 4H); Mass (ESI) m/z 302.7 (M$^+$).

Example 9

Preparation of N1-2-(thiophen-2-ylethyl)-N2-2-ethylphenyl biguanide hydrochloride $^1$H NMR (300 MHz, DMSO-$d_6$) δ 7.23-7.38 (m, 6H), 6.90-6.91 (m, 2H), 3.27-3.39 (m, 4H), 2.98-3.00 (m, 2H), 2.77-2.79 (m, 2H); Mass (ESI) m/z 316.5 (M$^+$).

Example 10

Preparation of N1-2-(thiophen-2-ylethyl)-N2-methyl biguanide hydrochloride (isomer)

$^1$H NMR (300 MHz, DMSO-$d_6$) δ 7.34-7.36 (m, 1H), 6.92-6.95 (m, 2H), 3.55-3.59 (t, 2H, J=7.4), 3.27-3.28 (m, 3H), 3.06-3.11 (t, 2H, J=7.4); mp 185.0-199.5° C.

Example 11

Preparation of N1-2-(thiophen-2-ylethyl)-N2-methyl biguanide hydrochloride (isomer)

$^1$H NMR (300 MHz, DMSO-$d_6$) δ 7.32-7.35 (m, 1H), 6.90-6.93 (m, 2H), 3.28-3.53 (m, 2H), 2.95-3.16 (m, 2H), 2.80 (s, 3H).

Example 12

Preparation of N1-2-(thiophen-2-ylethyl)-N2-methyl biguanide hydrochloride (isomer)

$^1$H NMR (300 MHz, DMSO-$d_6$) δ 7.32-7.33 (m, 1H), 6.88-6.91 (m, 2H), 3.47-3.51 (m, 2H), 3.01-3.05 (m, 2H), 2.90 (s, 3H).

Example 13

Preparation of N1-2-(thiophen-2-ylethyl)-N2-propyl biguanide hydrochloride $^1$H NMR (300 MHz, DMSO-$d_6$) δ 7.30-7.40 (m, 1H), 6.89-6.83 (m, 2H), 3.34-3.45 (m, 2H), 2.93-3.01 (m, 4H), 1.41-1.50 (m, 2H), 0.78-0.85 (m, 3H).

Example 14

Preparation of N1-2-(thiophen-2-ylethyl)-N2-(3-trifluoromethyl)phenyl biguanide hydrochloride $^1$H NMR (300 MHz, DMSO-d$_6$) δ 7.47-7.22 (m, 5H), 6.92-6.86 (m, 2H), 3.38-3.40 (m, 2H), 2.97-3.02 (m, 2H); mp 129-131° C.

Example 15

Preparation of N1-2-(thiophen-2-ylethyl)-N2-(4-methoxy)phenyl biguanide hydrochloride $^1$H NMR (300 MHz, D$_2$O) δ 7.26-7.28 (m, 1H), 7.02-7.05 (m, 2H), 6.85-6.92 (m, 4H), 3.70 (s, 3H), 3.32-3.37 (m, 2H), 2.98-3.10 (m, 2H); mp 127-129° C.

Example 16

Preparation of N1-2-(thiophen-2-ylethyl)-N2-(2,5-dimethoxy)phenyl biguanide hydrochloride $^1$H NMR (300 MHz, D$_2$O) δ 7.26-7.29 (m, 1H), 6.83-6.94 (m, 3H), 6.67-6.70 (m, 2H), 3.62 (s, 3H), 3.68 (s, 3H), 3.33 (t, 2H, J=7.0), 2.98 (t, 2H, J=7.1); mp 179-181° C.

Example 17

Preparation of N1-2-(thiophen-2-ylethyl)-N2-(3,4,5-trimethoxy)phenyl biguanide hydrochloride $^1$H NMR (300 MHz, D$_2$O) δ 7.25-7.23 (m, 2H), 6.91-6.85 (m, 3H), 3.65 (s, 6H), 3.55 (s, 3H), 3.36 (t, 2H, J=7.0 Hz), 2.97 (t, 2H, J=7.3 Hz); mp 92-94° C.

Example 18

Preparation of N1-2-(thiophen-2-ylethyl)-N2-(4-fluorophenyl) biguanide hydrochloride $^1$H NMR (300 MHz, D$_2$O) δ 7.29-7.31 (m, 1H, J=4.5 Hz), 7.14-7.11 (m, 4H), 6.94-6.89 (m, 2H), 3.34 (t, 2H, J=7.5 Hz), 3.00 (t, 2H, J=7.3 Hz); mp 83-85° C.

Example 19

Preparation of N1-2-(thiophen-2-ylethyl)-N2-(4-methylphenyl) biguanide hydrochloride $^1$H NMR (300 MHz, D$_2$O) δ 7.28-7.31 (m, 1H), 7.13-7.16 (m, 2H), 6.88-6.96 (m, 4H), 3.38 (t, 2H, J=7.2 Hz), 3.01 (t, 2H, J=7.2 Hz), 2.21 (s, 3H); mp 97-99° C.

Example 20

Preparation of N1-2-(thiophen-2-ylethyl)-N2-phenyl biguanide hydrochloride $^1$H NMR (300 MHz, DMSO-d$_6$) δ 7.30-7.24 (m, 3H), 7.10-7.07 (m, 3H), 6.94-6.88 (m, 2H), 3.38 (t, 2H, J=7.3 Hz), 3.01 (t, 2H, J=7.2 Hz).

Example 21

Preparation of N1-2-(thiophen-2-ylethyl)-N2-cyclopentyl biguanide hydrochloride $^1$H NMR (300 MHz, D$_2$O) δ 7.27-7.26 (m, 1H), 6.92-6.90 (m, 1H), 6.85-6.83 (m, 1H), 3.75-3.79 (m, 1H), 3.28 (t, 2H, J=7.2 Hz), 2.94 (t, 2H, J=7.2 Hz), 1.82-1.73 (m, 2H), 1.60-1.53 (m, 2H), 1.49-1.33 (m, 4H).

Example 22

Preparation of N1-2-(thiophen-2-ylethyl)-N2-cycloheptyl biguanide hydrochloride $^1$H NMR (300 MHz, D$_2$O) δ 7.28-7.30 (m, 1H), 6.86-6.94 (m, 2H), 3.48-3.51 (m, 1H), 3.28-3.31 (m, 2H), 2.98-3.05 (m, 2H), 1.54-1.60 (m, 2H), 1.13-1.45 (m, 10H).

Example 23

Preparation of N1-2-(thiophen-2-ylethyl)-N2-pentyl biguanide hydrochloride $^1$H NMR (300 MHz, DMSO-d$_6$) δ 7.33 (m, 1H), 6.90-6.95 (m, 2H), 3.49-3.55 (m, 2H), 3.21-3.40 (m, 2H), 3.00-3.15 (m, 2H), 1.22-1.50 (m, 6H), 0.79-0.87 (m, 3H).

Example 24

Preparation of N1-2-(thiophen-2-ylethyl)-N2-methoxyethyl biguanide hydrochloride $^1$H NMR (300 MHz, D$_2$O) δ 7.32-7.33 (m, 1H), 6.93-6.95 (m, 1H), 6.86-6.88 (m, 1H), 3.36-3.33 (m, 4H), 3.21 (s, 5H), 2.97-3.02 (m, 2H).

Example 25

Preparation of N1-2-(thiophen-2-ylethyl)-N2-butyl biguanide hydrochloride $^1$H NMR (300 MHz, DMSO-d$_6$) δ 7.30 (m, 1H), 6.93-6.88 (m, 2H), 3.50 (m, 2H), 2.79-3.10 (m, 4H), 1.16-1.45 (m, 4H), 0.82-0.86 (m, 3H).

Example 26

Preparation of N1-2-(thiophen-2-ylethyl)-N2-butyl biguanide hydrochloride (isomer)

$^1$H NMR (300 MHz, DMSO-d$_6$) δ 7.19-7.30 (m 1H), 6.93-6.88 (m, 2H), 3.30-3.40 (m, 2H), 2.70-3.29 (m, 4H), 1.15-1.60 (m, 4H), 0.83-0.88 (m, 3H).

Example 27

Preparation of N1-2-(thiophen-2-ylethyl)-N2-(3-methylphenyl) biguanide hydrochloride $^1$H NMR (300 MHz, D$_2$O) δ 7.29-7.31 (m, 1H), 7.13-7.16 (m, 2H), 6.88-6.95 (m, 4H), 3.37-3.41 (m, 2H), 2.99-3.03 (m, 2H), 2.21 (s, 3H).

Example 28

Preparation of N1-2-(thiophen-2-ylethyl)-N2-(4-t-butylphenyl) biguanide hydrochloride $^1$H NMR (300 MHz, D$_2$O) δ 7.27-7.30 (m, 3H), 7.01-7.04 (d, 2H, J=6.9), 6.87-6.94 (m, 2H), 3.36-3.40 (m, 2H), 2.98-3.03 (m, 2H), 1.14 (s, 9H); mp 215.2-224.1° C.

Example 29

Preparation of N1-2-(thiophen-2-ylethyl)-N2-(4-hexylphenyl) biguanide hydrochloride $^1$H NMR (300 MHz, DMSO-d$_6$) δ 7.34-7.36 (m, 1H), 7.04-7.11 (m, 4H), 6.87-6.97 (m, 2H), 3.32-3.43 (m, 2H), 2.91-3.04 (m, 2H), 2.47-2.50 (m, 2H) 1.49-1.51 (m, 2H), 1.25-1.35 (m, 6H), 0.81-0.85 (s, 3H); mp 155.8-160.8° C.

Example 30

Preparation of N1-2-(thiophen-2-ylethyl)-N2-(4-methoxyphenyl) biguanide hydrochloride (isomer)

$^1$H NMR (300 MHz, D$_2$O) δ 7.25-7.27 (m, 1H), 7.02-7.05 (m, 2H), 6.84-6.92 (m, 4H), 3.66 (s, 3H), 3.36-3.40 (m, 2H), 2.97-3.01 (m, 2H); mp 98.6-99.2° C.

Example 31

Preparation of N1-2-(thiophen-2-ylethyl)-N2-(2,5-dimethoxyphenyl) biguanide hydrochloride $^1$H NMR (300 MHz, D$_2$O) δ 7.33-7.34 (m, 1H), 6.91-6.97 (m, 4H), 6.65-6.70 (m, 1H), 3.73 (s, 3H), 3.70 (s, 3H), 3.33-3.39 (t, 2H, J=6.9), 2.95-3.03 (t, 2H, J=6.9).

Example 32

Preparation of N1-2-(thiophen-2-ylethyl)-N2-(3,5-dimethoxyphenyl) biguanide hydrochloride $^1$H NMR (300 MHz, D$_2$O) δ 7.28-7.30 (m, 1H), 6.88-6.95 (m, 2H), 6.21-6.29 (m, 3H), 3.66 (s, 6H), 3.37-3.42 (t, 2H, J=6.9), 2.99-3.04 (t, 2H, J=6.9); mp 162.8-167.1° C.

Example 33

Preparation of N1-2-(thiophen-2-ylethyl)-N2-(4-bromophenyl) biguanide hydrochloride $^1$H NMR (300 MHz, D$_2$O) δ 7.39-7.45 (m, 2H), 7.24-7.27 (m, 1H), 7.02-7.05 (m, 2H), 6.84-6.95 (m, 2H), 3.35-3.42 (m, 2H), 2.96-3.05 (m, 2H); mp 126.8-133.7° C.

Example 34

Preparation of N1-2-(thiophen-2-ylethyl)-N2-(3-bromophenyl) biguanide hydrochloride $^1$NMR (300 MHz, D$_2$O) δ 7.20-7.33 (m, 4H), 7.08-7.11 (m, 1H), 6.85-6.95 (m, 2H), 3.36-3.41 (m, 2H), 2.95-3.05 (m, 2H); mp 107.1-111.6° C.

Example 35

Preparation of N1-2-(thiophen-2-ylethyl)-N2-(4-phenylphenyl) biguanide hydrochloride $^1$H NMR (300 MHz, D$_2$O) δ 7.57-7.63 (m, 4H), 7.38-7.44 (m, 2H), 7.19-7.36 (m, 4H), 6.83-6.96 (m, 2H), 3.38-3.45 (m, 2H), 2.90-3.07 (m, 2H); mp 145.8-150.6° C.

Example 36

Preparation of N1-2-(thiophen-2-ylethyl)-N2-(4-phenoxyphenyl) biguanide hydrochloride $^1$H NMR (300 MHz, DMSO-d$_6$) δ 7.27-7.37 (m, 3H), 7.09-7.14 (m, 3H), 6.88-6.94 (m, 6H), 3.38 (t, 2H, J=7.2 Hz), 3.01 (t, 2H, J=7.2 Hz); mp 87.1-96.0° C.

Example 37

Preparation of N1-2-(thiophen-2-ylethyl)-N2-(4-bromobenzyl) biguanide hydrochloride $^1$H NMR (300 MHz, D$_2$O) δ 7.43-7.50 (m, 2H), 7.22-7.28 (m, 1H), 7.09-7.17 (m, 2H), 6.75-6.93 (m, 2H), 4.23 (s, 2H), 3.29-3.33 (m, 2H), 2.93-3.03 (m, 2H); mp 102.1-103.5° C.

Example 38

Preparation of N1-2-(thiophen-2-ylethyl)-N2-(4-methoxybenzyl) biguanide hydrochloride $^1$H NMR (300 MHz, D$_2$O) δ 7.24-7.26 (d, 1H, J=6.7 Hz), 7.11-7.16 (d, 2H, J=6.7 Hz), 6.80-6.91 (m, 4H), 4.18 (s, 2H), 3.66 (s, 3H), 3.28-3.33 (t, 2H, J=7.2 Hz), 2.92-3.02 (t, 2H, J=7.2 Hz).

Example 39

Preparation of N1-2-(thiophen-2-ylethyl)-N2-(3,5-dichlorophenyl) biguanide hydrochloride $^1$H NMR (300 MHz, D$_2$O) δ 7.21-7.27 (m, 2H), 7.10 (s, 2H), 6.88-6.95 (m, 2H), 3.34-3.40 (m, 2H), 3.03-3.08 (m, 2H).

Example 40

Preparation of N1-2-(thiophen-2-ylethyl)-N2-(4-methylbenzyl) biguanide hydrochloride $^1$H NMR (300 MHz, D$_2$O) δ 7.24-7.27 (m, 1H), 7.079-7.09 (m, 3H), 6.81-6.91 (m, 3H), 4.34-4.37 (m, 2H), 3.28-3.33 (m, 2H), 2.96-3.04 (m, 2H), 2.25 (s, 3H).

Example 41

Preparation of N1-2-(thiophen-2-ylethyl)-N2-isopropyl biguanide hydrochloride $^1$H NMR (300 MHz, DMSO-d$_6$) δ 7.34-7.36 (m, 1H), 6.90-6.99 (m, 2H), 3.70-3.75 (m, 1H), 3.35-3.40 (m, 2H), 2.95-3.00 (m, 2H), 1.06-1.08 (m, 6H).

Example 42

Preparation of -2-(thiophen-2-ylethyl)-N2-isobutyl biguanide hydrochloride $^1$H NMR (300 MHz, D$_2$O) δ 7.30-7.32 (m, 1H), 6.90-6.95 (m, 2H), 3.34-3.40 (m, 2H), 3.99-3.04 (m, 2H), 2.90-2.98 (m, 2H), 1.73-1.77 (m, 1H), 0.81-0.99 (m, 6H).

Example 43

Preparation of N1-2-(thiophen-2-ylethyl)-N2-cyclopropylmethyl biguanide hydrochloride $^1$H NMR (300 MHz, D$_2$O) δ 7.30-7.31 (m, 1H), 6.91-6.94 (m, 2H), 3.36-3.41 (m, 2H), 3.05-2.97 (m, 4H), 0.94-0.97 (m, 1H), 0.46-0.43 (m, 2H), 0.19-0.18 (m, 2H).

Example 44

Preparation of N1-2-(thiophen-2-ylethyl)-N2-allyl biguanide hydrochloride $^1$H NMR (300 MHz, DMSO-d$_6$) δ 7.28-7.30 (m, 1H), 6.90-6.93 (m, 2H), 5.73-5.80 (m, 1H), 5.10-5.20 (m, 2H), 3.77-3.78 (m, 2H), 3.39-3.43 (m, 2H), 2.99-3.04 (m, 2H); mp 97-99° C.

Example 45

Preparation of N1-2-(3-methylthiophen-2-ylethyl)-N2-methyl biguanide hydrochloride (45-1) Preparation of (3-methylthiophen-2-yl)methanol (Compound 3)

3-Methyl-2-thiophen-carboxaldehyde (1.00 g, 7.93 mmol) was dissolved in methanol (16 mL), and the reaction mixture was cooled to 0° C., and then sodium borohydride (0.60 g, 15.86 mmol) was added. The reaction mixture was stirred at room temperature for about 30 min, and water (30 mL) was sequentially added to the mixture. The resulting mixture was extracted with ethyl acetate. The extract was washed with saline, dried over sodium sulfate, and concentrated. The residue was purified by flash column chromatography (ethyl acetate:hexanes=20:80), to obtain the title compound (0.89 g, 88%).

$^1$H NMR (300 MHz, CDCl$_3$) δ 7.17 (d, 1H, thiophene), 6.84 (d, 1H, thiophene), 4.76 (d, 2H, J=4.92 Hz, CH$_2$), 2.25 (s, 3H, CH$_3$), 1.66 (t, 1H, J=5.43 Hz, OH); IR (neat): 3320, 3100, 3060, 2918, 2861, 1555, 1430, 1383, 1368, 1353, 1300, 1231, 1171, 1032, 996, 932, 876, 832, 703, 663 cm−1; MS (ESI+) m/z 128.19 [M+].

(45-2) Preparation of 2-(3-methylthiophen-2-yl) acetonitrile (Compound V)

Thionyl chloride (0.85 mL, 11.70 mmol) was slowly added dropwise to dichloromethane (5 mL) comprising (3-methylthiophen-2-yl)methanol obtained in step (45-1) (0.50 g 3.90 mmol). The reaction mixture was stirred at room temperature for about 30 minutes, and concentrated under a reduced pressure to obtain chloride (compound IV). The concentrate was dissolved in dimethyl sulfoxide (2 mL). Sodium cyanide (0.57 g, 11.70 mmol) was added thereto and stirred at room temperature for 1 hr. Water (30 mL) was sequentially added to the reaction mixture, and the resulting solution was extracted with ethyl acetate. The organic layer was washed with brine, dried over sodium sulfate, and concentrated. The residue was purified by flash column chromatography (ethyl acetate:hexane=20:80), to obtain the title compound (0.39 g, 56%).

$^1$NMR (300 MHz, CDCl$_3$) δ 7.16 (d, 1H, thiophene), 6.84 (d, 1H, thiophene), 3.78 (s, 2H, CH$_2$), 2.24 (s, 3H, CH$_3$); IR (neat): 3098, 2917, 2248, 1557, 1432, 1409, 1383, 1367, 1298, 1237, 1159, 1083, 1023, 952, 915, 879, 855, 828, 738, 706, 664 cm$^{-1}$.

(45-3) Preparation of 2-(3-methylthiophen-2-yl) ethane amine (Compound VI)

Nickel chloride (0.95 g, 0.73 mmol) was slowly added dropwise to the solution of 2-(3-methylthiophen-2-yl) acetonitrile obtained in step (45-2) (0.10 g 0.73 mmol) in ethanol (3 mL). To a reaction mixture was added portion wise sodium borohydride (0.83 g, 2.19 mmol), and was stirred at room temperature. Water (30 mL) was sequentially added to the mixture, and the resulting mixture was extracted with ethyl acetate. The organic layer was washed with brine, dried over sodium sulfate, and concentrated. The residue was purified by flash column chromatography (dichloro methane:methanol=8:2), to obtain the title compound (51 mg, 50%).

$^1$H NMR (300 MHz, CDCl$_3$) δ 7.09 (d, 1H, thiophene), 6.80 (d, 1H, thiophene), 3.21 (s, 4H, 2×CH$_2$), 2.21 (s, 3H, CH$_3$).

(45-4) Preparation of N1-2-(3-methylthiophen-2-yl)-N2-methyl thiourea

The procedure of step (1-1) of Example 1 was repeated except for using the compound obtained in step (45-3) (1.4 g, 10.2 mmol) to obtain the title compound (1.9 g, 87%).

$^1$H NMR (300 MHz, CDCl$_3$) δ 7.06 (d, 1H, J=5.1 Hz), 6.81 (d, 1H, J=5.1 Hz), 6.40 (br s, 1H), 6.00 (br s, 1H), 3.74 (m, 2H), 3.05 (m, 2H), 2.89 (m, 3H), 2.20 (s, 3H).

(45-5) Preparation of N1-2-(3-methylthiophen-2-ylethyl)-N2-methyl biguanide hydrochloride The procedure of step (1-2) of Example 1 was repeated except for using the compound obtained in step (45-4) (1.1 g, 5.10 mmol) to obtain the title compound (0.23 g, 16%).

$^1$H NMR (300 MHz, D$_2$O) δ 7.02 (d, 1H, J=5.1 Hz), 6.64 (d, 1H, J=5.1 Hz), 3.04-3.06 (m, 2H), 2.72-2.74 (m, 2H), 2.48 (s, 3H), 1.93 (s, 3H).

Example 46

Preparation of N1-2-(5-ethylthiophen-2-ylethyl)-N2-methyl biguanide hydrochloride The procedure of Example 1 was repeated except for using the compound, which corresponds to a desired compound, instead of 3-methyl-2-thiophen-carboxaldehyde in step (45-1) of Example 45, to obtain the desired compound.

$^1$H NMR (300 MHz, D$_2$O) δ 6.40-6.43 (m, 2H), 3.07-3.09 (m, 2H), 2.67-2.69 (m, 2H), 2.46-2.49 (m, 5H), 0.91-0.96 (m, 3H).

TEST EXAMPLES

The pharmacological activities of the compounds prepared in Examples 1 to 46 were determined as described in the following Test Examples 1 to 4. Several tests were conducted three times on each of five plates which were grouped by the compounds of Examples 1 to 9, Examples 10 to 12, Examples 13 to 22, Examples 23 to 39, and Examples 40 to 46, and average values were calculated from results of the tests. 2 mM metformin was used as a comparative compound for each of the plates (control group). In this case, even though metformin having the same concentration was used, test average values obtained were more or less different from each other due to different measuring environments among the plates.

The glucose absorption ability was measured using insulin and the control group simultaneously, and values of more than 200% in consideration of deviations on the basis of cell-based experiments are determined to have a glucose absorption ability.

Test Example 1

Measurement of Cholesterol Synthesis Inhibitory Ability

A cholesterol synthesis inhibitory ability, which is an important function of AMPK (AMP-activated protein kinase), was measured using HepG2 cells (ATCC: American Type Culture Collection) as a hepatic cell model according to the following procedure.

The hepatic cell model HepG2 cells were cultured in 1% serum-containing media (DMEM (Gibco), FBS (Gibco)) for 24 hours, and then treated with 100 μM or 500 μM of each of the compounds prepared in Examples for 24 hours. Then, the cells were disrupted with a lysis solution (0.1 M potassium phosphate, pH 7.4, 0.05 M NaCl, 5 mM cholic acid, 0.1% Triton X-100 (Sigma)). To the disrupted cells was added the same volume of a reaction solution (2 U/mL of a cholesterol oxidizing agent, 2 U/mL of a peroxidase, 0.2 U/mL of a cholesterol esterase, and 300 μM of Amplex red as a fluorescent factor (Molecular Probe)), which was allowed to react at 37° C. for 30 minutes. After completion of the reaction, the content of cholesterol formed in the cell lysates was measured at a wavelength of 560/590 nm (ex/em) using a fluorescence microscope.

A lower measurement value means an increased cholesterol synthesis inhibitory ability. If the inventive compounds (a 100 μM or 500 μM concentration) show values less than the value of the control group (a 2 mM concentration), it is understood that they are much superior to the control group by comparison of the used amounts. For example, the compound of Example 1 showed a lower value than the control group at a concentration of 100 μM, suggesting that the effect in inhibiting synthesis of the compound was better by at least 20 times than that of the control group.

Test Example 2

Measurement of Triglyceride

HepG2 cells (ATCC: American Type Culture Collection) were cultured in 1% serum-containing media (DMEM (Gibco), FBS (Gibco)) for 24 hours, and then treated with 100 μM or 500 μM of each of the compounds prepared in Examples for 24 hours. Then, the cells were disrupted with a lysis solution (0.1 M potassium phosphate, pH 7.4, 0.05 M NaCl, 5 mM cholic acid, 0.1% Triton X-100). To the disrupted cells was added the same volume of a reaction solution (0.76 U/mL of a glycerol kinase (Asan Pharmaceutical Co., Ltd.), 151333 U/mL of a peroxidase (Asan Pharmaceutical Co., Ltd.), 22.2 U/mL of a glycerol oxidizing agent (Asan Pharmaceutical Co., Ltd.), and 300 μM of Amplex red as a fluorescent factor (Molecular Probe)), which was allowed to react at 37° C. for 30 minutes. After completion of the reaction, the content of triglyceride formed in the cell lysates was measured at a wavelength of 560/590 nm (ex/em) using a fluorescence microscope.

A lower measurement value means an increased triglyceride synthesis inhibitory ability. If the inventive compounds (a 100 μM or 500 μM concentration) show values less than the value of the control group (a 2 mM concentration), it is understood that they are much superior to the control group by comparison of the used amounts. For example, the compound of Example 1 showed a lower value than the control group at a concentration of 100 μM, suggesting that the effect in inhibiting triglyceride synthesis of the compound was better by at least 20 times than that of the control group.

Test Example 3

Measurement of Gluconeogenesis Inhibitory Ability

HepG2 cells (ATCC: American Type Culture Collection) were cultured in 10% serum-containing high glucose media, transferred to no serum-containing low glucose media (DMEM (Gibco), FBS (Gibco)), and then treated with 100 μM of each of the compounds for 24 hours. Then, the cells were treated with 0.5 μCi $^{14}$C-lactate (Amersham Pharmacia) and 10 mM L-lactate (Sigma), and cultured for 4 hours. After cultivation, the media were removed therefrom, and the cells were washed with PBS, treated with 0.1N NaOH and kept at room temperature for 1 hour. Then, the cells were neutralized with 1N HCl, and the content of glucose formed in the cells was measured with a liquid scintillation counter.

A lower measurement value means an increased gluconeogenesis inhibitory ability. If the inventive compounds (a 100 μM concentration) show values less than the value of the control group (a 2 mM concentration), it is understood that they are much superior to the control group by comparison of the used amounts. For example, the compound of Example 1 showed a lower value than the control group at a concentration of 100 μM, suggesting that the effect in inhibiting gluconeogenesis of the compound was better by at least 20 times than that of the control group.

Test Example 4

Measurement of Glucose Absorption Ability

C2C12 cells (ATCC: American Type Culture Collection), a muscle cell model, were induced to differentiate into muscle cells in 2% bovine fetal serum-containing media (DMEM (Gibco), FBS (Gibco)) for 6 days. The C2C12 cells which differentiated into muscle cells were transferred to serum-free low glucose media (DMEM (Gibco), FBS (Gibco)), treated with 100 μM of each of the compounds, and then cultured with 1 μM of insulin for 24 hours. After cultivation, the cells were treated with 1 μCi $^{3}$H-deoxy-glucose (Amersham Pharmacia) and 10 μM deoxy-glucose (Sigma) at 37° C. for 15 minutes. The media were removed therefrom, and the cells were washed twice with PBS (phosphate buffered saline). The washed cells were treated with 0.1N NaOH and neutralized with 1N HCl. The content of glucose absorbed into the cells was measured with a liquid scintillation counter.

A higher measurement value means a stronger ability to reduce insulin resistance. The compound of Example 1 showed a value similar to the control group at a concentration of 100 μM, suggesting that the glucose absorption effect of the compound was better by about 20 times than that of the control group.

TABLE 1

| Ex. | Triglyceride (100 uM) | | Triglyceride (500 uM) | | Cholesterol (100 uM) | | Cholesterol (500 uM) | | Gluconeogenesis inhibition (100 uM) | | Glucose absorption (100 uM) | |
|---|---|---|---|---|---|---|---|---|---|---|---|---|
| | Aver. | S.D. | Aver. | S.D. | Aver. | S.D. | Aver. | S.D. | Aver. | S.D. | Aver. | S.D. |
| 1 | 56.70 | 4.08 | 54.57 | 8.62 | 45.18 | 8.80 | 30.51 | 11.3 | 48.92 | 4.03 | 322.7 | 0.44 |
| 2 | 29.21 | 2.82 | −1.92 | 3.58 | 63.63 | 25.3 | 55.38 | 8.48 | 68.28 | 23.81 | 10.46 | 0.90 |
| 3 | 5.28 | 1.75 | −6.37 | 0.19 | 30.90 | 0.99 | 31.14 | 9.71 | 3.73 | 0.49 | 15.10 | 2.52 |
| 4 | 22.80 | 2.09 | 3.22 | 5.88 | 33.81 | 3.85 | 51.74 | 9.38 | 26.40 | 3.71 | 14.31 | 1.41 |
| 5 | 65.03 | 3.08 | 41.59 | 3.62 | 49.29 | 4.16 | 41.36 | 3.08 | 58.50 | 9.23 | 350.4 | 8.20 |
| 6 | 51.00 | 6.37 | −1.71 | 0.29 | 30.58 | 1.33 | 0.51 | 3.91 | 33.59 | 2.07 | 56.15 | 34.25 |
| 7 | 74.43 | 6.97 | 16.49 | 2.20 | 42.51 | 2.27 | 2.79 | 3.21 | 39.98 | 6.89 | 21.59 | 5.91 |
| 8 | 77.65 | 2.46 | 30.78 | 3.85 | 37.77 | 7.16 | 7.28 | 4.82 | 81.27 | 11.83 | 243.3 | 15.64 |
| 9 | 74.99 | 4.62 | 19.51 | 2.82 | 39.25 | 3.31 | 7.55 | 3.05 | 74.23 | 10.44 | 252.6 | 12.74 |

| | Triglyceride | | Cholesterol | | Gluconeogenesis inhibition | | Glucose absorption | |
|---|---|---|---|---|---|---|---|---|
| | Aver. | St. Dev. | Aver. | St. Dev. | Aver. | St. Dev. | Aver. | St. Dev. |
| Metformin (2 mM) | 69.58 | 4.70 | 74.50 | 3.05 | 59.14 | 4.44 | 335.45 | 3.50 |

| Ex. | Triglyceride (100 uM) | | Cholesterol (100 uM) | | Gluconeogenesis Inhibition (100 μM) | | Glucose Absorption (100 μM) | |
|---|---|---|---|---|---|---|---|---|
| | Aver. | St. Dev. | Aver. | St. Dev. | Aver. | St. Dev. | Aver. | St. Dev. |
| 10 | 76.16 | 3.12 | 52.29 | 4.14 | 5.72 | 6.45 | 6.91 | 0.42 |
| 11 | 74.98 | 1.76 | 71.14 | 2.05 | 25.03 | 0.34 | 321.21 | 15.07 |
| 12 | 67.43 | 0.71 | 69.94 | 1.28 | 13.05 | 1.03 | 221.61 | 3.53 |

| | Triglyceride | | Cholesterol | | Gluconeogenesis inhibition | | Glucose absorption | |
|---|---|---|---|---|---|---|---|---|
| | Aver. | St. Dev. | Aver. | St. Dev. | Aver. | St. Dev. | Aver. | St. Dev. |
| Metformin (2 mM) | 73.61 | 0.78 | 85.91 | 4.18 | 53.09 | 1.79 | 291.63 | 2.13 |

| Ex. | Triglyceride (100 uM) | | Triglyceride (500 uM) | | Cholesterol (100 uM) | | Cholesterol (500 uM) | | Gluconeogenesis inhibition (100 uM) | | Glucose absorption (100 uM) | |
|---|---|---|---|---|---|---|---|---|---|---|---|---|
| | Aver. | S.D. | Aver. | S.D. | Aver. | S.D. | Aver. | S.D. | Aver. | S.D. | Aver. | S.D. |
| 13 | 59.3 | 3.19 | 48.9 | 2.26 | 77.1 | 0.94 | 61.7 | 4.54 | 73.51 | 1.85 | 110.2 | 2.19 |
| 14 | 11.8 | 0.12 | 13.2 | 1.42 | 23.3 | 1.95 | 41.4 | 3.25 | 8.75 | 0.78 | 4.38 | 0.03 |
| 15 | 76.6 | 1.79 | 41.4 | 2.27 | 67.3 | 1.31 | 39.7 | 1.71 | 86.69 | 0.95 | 124.3 | 20.0 |
| 16 | 73.8 | 1.78 | 51.3 | 5.56 | 85.0 | 2.80 | 58.5 | 1.08 | 68.89 | 0.59 | 147.3 | 15.0 |
| 17 | 86.2 | 3.11 | 79.4 | 0.93 | 87.2 | 1.21 | 57.5 | 0.57 | 95.56 | 0.44 | 165.2 | 24.1 |
| 18 | 67.0 | 0.72 | 39.5 | 0.79 | 50.3 | 2.34 | 23.4 | 7.63 | 86.69 | 7.23 | 88.16 | 8.3 |
| 19 | 67.7 | 1.71 | 46.4 | 0.81 | 52.9 | 1.52 | 29.6 | 6.83 | 74.32 | 5.39 | 89.16 | 14.1 |
| 20 | 67.5 | 3.55 | 57.6 | 1.70 | 45.7 | 3.64 | 18.3 | 0.50 | 87.36 | 0.54 | 125.4 | 6.1 |
| 21 | 80.5 | 8.51 | 85.6 | 12.7 | 68.2 | 4.05 | 45.8 | 2.55 | 97.66 | 1.70 | 174.8 | 36.1 |
| 22 | 77.8 | 10.8 | 78.9 | 3.55 | 69.8 | 2.96 | 44.4 | 0.55 | 96.63 | 0.47 | 173.8 | 25.8 |

| | Triglyceride | | Cholesterol | | Gluconeogenesis inhibition | | Glucose absorption | |
|---|---|---|---|---|---|---|---|---|
| | Aver. | St. Dev. | Aver. | St. Dev. | Aver. | St. Dev. | Aver. | St. Dev. |
| Metformin (2 mM) | 70.05 | 7.44 | 70.69 | 5.37 | 78.33 | 4.63 | 170.94 | 34.76 |

| Ex. | Triglyceride (100 uM) | | Triglyceride (500 uM) | | Cholesterol (100 uM) | | Cholesterol (500 uM) | | Gluconeogenesis inhibition (100 uM) | | Glucose absorption (100 uM) | |
|---|---|---|---|---|---|---|---|---|---|---|---|---|
| | Aver. | S.D. | Aver. | S.D. | Aver. | S.D. | Aver. | S.D. | Aver. | S.D. | Aver. | S.D. |
| 23 | 13.83 | 1.36 | 17.16 | 4.48 | 11.05 | 7.53 | 15.66 | 1.52 | 2.96 | 0.23 | 0.00 | 0.00 |
| 24 | 77.91 | 2.45 | 71.93 | 4.01 | 92.58 | 3.64 | 75.75 | 5.27 | 78.89 | 3.68 | 114.91 | 10.20 |
| 25 | 19.21 | 2.64 | 17.02 | 1.78 | 32.66 | 4.36 | 19.87 | 9.01 | 0.00 | 0.00 | 2.76 | 0.95 |

TABLE 1-continued

| | | | | | | | | | | | |
|---|---|---|---|---|---|---|---|---|---|---|---|
| 26 | 47.59 | 5.12 | 30.67 | 2.75 | 43.20 | 1.43 | 13.28 | 3.08 | 81.70 | 5.80 | 18.34 | 6.59 |
| 27 | 46.45 | 0.09 | 20.64 | 0.87 | 33.26 | 1.79 | 28.82 | 6.97 | 56.42 | 5.83 | 12.91 | 0.85 |
| 28 | 15.55 | 2.00 | 15.21 | 3.73 | 27.49 | 2.84 | 26.60 | 1.77 | 2.57 | 0.13 | 4.29 | 1.06 |
| 29 | 8.04 | 0.53 | 42.57 | 2.20 | 30.10 | 1.79 | 119.39 | 1.13 | 1.26 | 1.78 | 3.96 | 0.00 |
| 30 | 91.91 | 2.09 | 48.42 | 2.51 | 73.64 | 5.79 | 26.15 | 0.69 | 105.18 | 7.64 | 148.42 | 1.48 |
| 31 | 81.74 | 9.20 | 57.32 | 3.10 | 75.67 | 4.31 | 49.39 | 2.02 | 96.29 | 2.23 | 168.20 | 3.55 |
| 32 | 70.80 | 5.80 | 28.47 | 2.68 | 48.02 | 0.58 | 26.70 | 3.38 | 152.19 | 6.97 | 11.68 | 0.13 |
| 33 | 29.12 | 1.51 | 27.48 | 1.87 | 24.52 | 1.99 | 31.66 | 5.58 | 17.03 | 1.45 | 14.24 | 8.87 |
| 34 | 26.57 | 1.55 | 19.49 | 0.70 | 26.00 | 2.80 | 32.53 | 0.88 | 4.96 | 0.46 | 6.05 | 0.81 |
| 35 | 18.94 | 0.81 | 14.92 | 0.26 | 28.27 | 2.31 | 30.49 | 0.22 | 109.62 | 6.94 | 35.00 | 3.02 |
| 36 | 20.95 | 1.65 | 17.89 | 2.26 | 31.22 | 2.57 | 34.74 | 1.72 | 1.54 | 2.18 | 4.50 | 0.11 |
| 37 | 61.41 | 3.28 | 20.15 | 1.52 | 28.36 | 2.40 | 30.84 | 2.25 | 89.96 | 4.50 | 7.71 | 0.88 |
| 38 | 100.89 | 8.04 | 84.10 | 8.22 | 80.35 | 3.00 | 44.72 | 4.75 | 120.13 | 1.43 | 195.22 | 0.77 |
| 39 | 73.50 | 3.40 | 72.66 | 3.64 | 69.65 | 2.63 | 61.03 | 0.85 | 13.04 | 0.01 | 188.26 | 18.07 |

| | Triglyceride | | Cholesterol | | Gluconeogenesis inhibition | | Glucose absorption | |
|---|---|---|---|---|---|---|---|---|
| | Aver. | St. Dev. | Aver. | St. Dev. | Aver. | St. Dev. | Aver. | St. Dev. |
| Metformin (2 mM) | 74.57 | 3.40 | 73.31 | 1.95 | 64.50 | 2.23 | 253.20 | 9.49 |

| | Triglyceride (100 uM) | | Triglyceride (500 uM) | | Cholesterol (100 uM) | | Cholesterol (500 uM) | | Gluconeogenesis inhibition (100 uM) | | Glucose absorption (100 uM) | |
|---|---|---|---|---|---|---|---|---|---|---|---|---|
| Ex. | Aver. | S.D. | Aver. | S.D. | Aver. | S.D. | Aver. | S.D. | Aver. | S.D. | Aver. | S.D. |
| 40 | 84.73 | 7.28 | 60.37 | 4.67 | 72.58 | 2.06 | 57.11 | 4.18 | 81.23 | 4.77 | 75.38 | 11.97 |
| 41 | 93.91 | 8.33 | 81.62 | 7.49 | 87.73 | 6.99 | 75.54 | 1.34 | 97.81 | 5.57 | 150.65 | 27.61 |
| 42 | 97.66 | 1.29 | 88.50 | 5.71 | 89.11 | 5.47 | 73.15 | 0.31 | 99.91 | 4.04 | 171.92 | 34.47 |
| 43 | 90.52 | 2.75 | 79.92 | 2.45 | 88.47 | 5.68 | 78.80 | 2.40 | 99.28 | 8.86 | 196.03 | 2.15 |
| 44 | 96.99 | 8.16 | 74.60 | 2.63 | 85.73 | 0.59 | 82.40 | 2.02 | 77.80 | 19.09 | 87.78 | 0.00 |
| 45 | 92.38 | 6.36 | 89.00 | 0.63 | 77.03 | 1.82 | 63.78 | 2.57 | 94.51 | 8.75 | 264.76 | 42.77 |
| 46 | 90.82 | 5.43 | 86.07 | 2.41 | 84.52 | 7.04 | 71.64 | 6.77 | 23.65 | 1.80 | 353.21 | 10.62 |

| | Triglyceride | | Cholesterol | | Gluconeogenesis inhibition | | Glucose absorption | |
|---|---|---|---|---|---|---|---|---|
| | Aver. | St. Dev. | Aver. | St. Dev. | Aver. | St. Dev. | Aver. | St. Dev. |
| Metformin (2 mM) | 81.14 | 3.17 | 65.31 | 17.17 | 39.79 | 0.83 | 365.22 | 23.75 |

While the invention has been described with respect to the specific embodiments, it should be recognized that various modifications and changes may be made by those skilled in the art to the invention which also fall within the scope of the invention as defined as the appended claims.

What is claimed is:

1. An N1-2-thiophen-2-ylethyl-N2-substituted biguanide derivative of formula (I) or a pharmaceutically acceptable salt thereof:

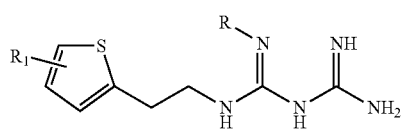

(I)

wherein,
R is $C_1$-$C_8$alkyl; allyl; $C_1$-$C_8$alkoxyalkyl; $C_3$-$C_7$cycloalkyl; $C_3$-$C_7$cycloalkyl$C_1$-$C_3$alkyl; substituted or non-substituted phenyl or phenyl$C_1$-$C_3$alkyl; substituted or non-substituted naphthyl or naphthyl$C_1$-$C_3$alkyl; or adamantyl; and
$R_1$ is hydrogen or $C_1$-$C_6$alkyl.

2. The compound or its pharmaceutically acceptable salt of claim 1, wherein
R is selected from the group consisting of methyl, ethyl, n-propyl, isopropyl, n-butyl, isobutyl, sec-butyl, tert-butyl, n-pentyl, n-hexyl, n-heptyl, n-octyl, allyl, adamantyl, methoxymethyl, methoxyethyl, methoxyethoxyethoxyethyl, ethoxymethyl, octyloxymethyl, cyclopropyl, cyclobutyl, cyclopentyl, cyclohexyl, cycloheptyl, cyclopropylmethyl, cyclobutylmethyl, cyclopentylmethyl, cyclohexylmethyl, cyclopropylethyl, cyclobutylethyl, cyclopentylethyl, cyclohexylethyl, cyclopropylpropyl, cyclobutylpropyl, cyclopentylpropyl, cyclohexylpropyl, benzyl, phenyl, naphthyl, 1-phenylethyl, 2-phenylethyl, 1-phenylpropyl, 2-phenylpropyl, 3-phenylpropyl, 1-naphthylmethyl, 2-naphthylmethyl, 1-naphthylethyl, and 2-naphthylethyl,
wherein, benzyl, phenyl, naphthyl, 1-phenylethyl, 2-phenylethyl, 1-phenylpropyl, 2-phenylpropyl, 3-phenylpropyl, 1-naphthylmethyl, 2-naphthylmethyl, 1-naphthylethyl, or 2-naphthylethyl optionally has one to six substituents, the substituents each independently being selected from the group consisting of halogen, hydroxy, nitro, cyano, $C_1$-$C_6$alkyl, $C_1$-$C_6$haloalkyl, $C_1$-$C_6$cycloalkyl, $C_6$-$C_{10}$aryl, $C_6$-$C_{10}$aryloxy, $C_1$-$C_6$alkoxy, $C_1$-$C_6$haloalkoxy, $C_3$-$C_6$cycloalkyloxy, C$_1$-C$_7$alkanoyl, carboxyl, carbamoyl, alkylamino, C$_2$-C$_7$sulfonate, sulfonamide, and C$_1$-C$_6$alkylthio; and R$_1$ is hydrogen, methyl, ethyl, propyl, butyl, pentyl, or hexyl.

3. The compound or its pharmaceutically acceptable salt of claim 2, wherein

R is ethyl, t-octyl, 1-naphthyl, hexyl, methyl, cyclohexyl, t-butyl, benzyl, 2-ethylphenyl, propyl, 3-trifluoromethylphenyl, 4-methoxyphenyl, 2,5-dimethoxyphenyl, 3,4,5-trimethoxyphenyl, 4-fluorophenyl, 4-methylphenyl, phenyl, cyclopentyl, cycloheptyl, pentyl, methoxyethyl, butyl, 3-methylphenyl, 4-t-butylphenyl, 4-hexylphenyl, 4-methoxyphenyl, 2,5-dimethoxyphenyl, 3,5-dimethoxyphenyl, 4-bromophenyl, 3-bromophenyl, 4-phenylphenyl, 4-phenoxyphenyl, 4-bromobenzyl, 4-methoxybenzyl, 3,5-dichlorophenyl, 4-methylbenzyl, isopropyl, isobutyl, cyclopropylmethyl, 2-(2-(2-methoxyethoxy)ethoxy)ethyl, or allyl; and R$_1$ is hydrogen, 3-methyl, or 5-ethyl.

4. The compound or its pharmaceutically acceptable salt of claim 1, wherein the pharmaceutically acceptable salt is a salt with an acid selected from the group consisting of formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, benzenesulfonic acid, p-toluenesulfonic acid, methansulfonic acid, hydrochloric acid, bromic acid, sulfuric acid, phosphoric acid, nitric acid, carbonic acid, and boric acid.

5. A method for preparing a compound of formula (I), which comprises the steps of:

1) subjecting a compound of formula (II) to a reaction with NaBH$_4$ in a solvent to form a compound of formula (III);
2) subjecting the compound of formula (III) to a reaction with thionyl chloride in an organic solvent to form a compound of formula (IV);
3) subjecting the compound of formula (IV) to a reaction with sodium cyanide in dimethylsulfoxide to form a compound of formula (V);
4) subjecting the compound of formula (V) to a reaction with sodium borohydride and a nickel chloride hydrate in a solvent to form a compound of formula (VI);
5) subjecting the compound of formula (VI) to a reaction with R-isothiocyanate in an organic solvent in the presence of a base to form a compound of formula (VIII); and
6) allowing the compound of formula (VIII) to be kept in a guanidine solution in the presence of mercuric oxide:

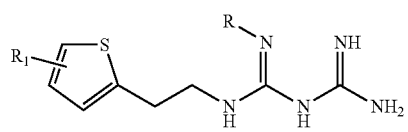

(I)

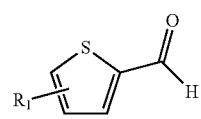

(II)

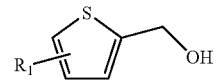

(III)

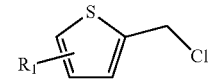

(IV)

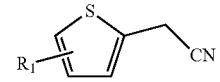

(V)

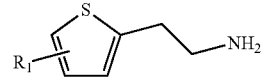

(VI)

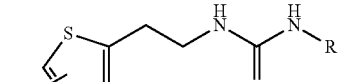

(VII)

wherein R is C$_1$-C$_8$alkyl; allyl; C$_1$-C$_8$alkoxyalkyl; C$_3$-C$_7$cycloalkyl; C$_3$-C$_7$cycloalkylC$_1$-C$_3$alkyl; substituted or non-substituted phenyl or phenylC$_1$-C$_3$alkyl; substituted or non-substituted naphthyl or naphthylC$_1$-C$_3$alkyl; or adamantyl; and R$_1$ is hydrogen or C$_1$-C$_6$alkyl.

6. A method for preparing a compound of formula (I), which comprises the steps of:

1) subjecting a compound of formula (II) to a reaction with NaBH4 in a solvent to form a compound of formula (III);
2) subjecting the compound of formula (III) to a reaction with thionyl chloride in an organic solvent to form a compound of formula (IV);
3) subjecting the compound of formula (IV) to a reaction with sodium cyanide in dimethylsulfoxide to form a compound of formula (V);
4) subjecting the compound of formula (V) to a reaction with sodium borohydride and a nickel chloride hydrate in a solvent to form a compound of formula (VI);
5) subjecting the compound of formula (VI) to a reaction with ethyl chloroformate in an organic solvent in the presence of carbon disulfide and a base to form a compound of formula (VII);
6) subjecting the compound of formula (VII) to a reaction with NH$_2$R in a solvent in the presence of a base to form a compound of formula (VIII); and
7) allowing the compound of formula (VIII) to be kept in a guanidine solution in the presence of mercuric oxide:

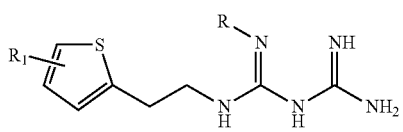

(I)

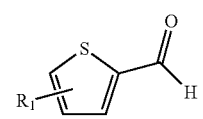

(II)

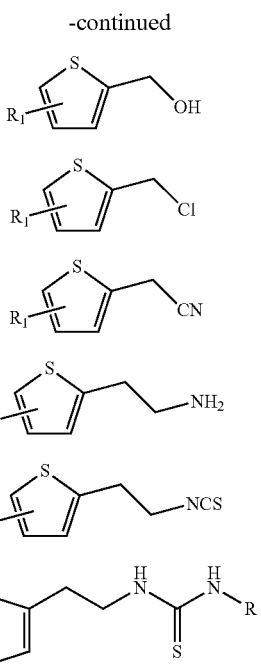

wherein
R is $C_1$-$C_8$alkyl; allyl; $C_1$-$C_8$alkoxyalkyl; $C_3$-$C_7$cycloalkyl; $C_3$-$C_7$cycloalkyl$C_1$-$C_3$alkyl; substituted or non-substituted phenyl or phenyl$C_1$-$C_3$alkyl; substituted or non-substituted naphthyl or naphthyl$C_1$-$C_3$alkyl; or adamantyl; and
$R_1$ is hydrogen or $C_1$-$C_6$alkyl.

7. The method of claim 5, wherein the base is selected from the group consisting of triethylamine, trimethylamine, diisopropylethylamine, and a mixture thereof; and the organic solvent is selected from the group consisting of dichloromethane, dichloroethane, dimethylformamide, and a mixture thereof.

8. The method of claim 6, wherein the base is selected from the group consisting of triethylamine, trimethylamine, diisopropylethylamine, and a mixture thereof; and the organic solvent is selected from the group consisting of dichloromethane, dichloroethane, dimethylformamide, and a mixture thereof.

9. A pharmaceutical composition, comprising the compound or its pharmaceutically acceptable salt of claim 1 as an active ingredient.

10. The pharmaceutical composition of claim 9, wherein the pharmaceutically acceptable salt is a salt with an acid selected from the group consisting of formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, benzenesulfonic acid, p-toluenesulfonic acid, methansulfonic acid, hydrochloric acid, bromic acid, sulfuric acid, phosphoric acid, nitric acid, carbonic acid, and boric acid.

11. A method for treating a metabolic syndrome, which comprises administering the compound or its pharmaceutically acceptable salt of claim 1 to a mammal in need thereof, wherein the metabolic syndrome is selected from the group consisting of cholesterol synthesis, gluconeogenesis, glucose absorption, and trigylceride synthesis.

12. A method for treating type 2 diabetes, which comprises administering the compound or its pharmaceutically acceptable salt of claim 1 to a mammal in need thereof.

* * * * *